United States Patent
Campbell et al.

(10) Patent No.: US 8,394,177 B2
(45) Date of Patent: Mar. 12, 2013

(54) METHOD OF SEPARATING COMPONENTS FROM A GAS STREAM

(75) Inventors: Timothy J. Campbell, East Lansing, MI (US); Farzaneh Teymouri, Okemos, MI (US); David K. Jones, Dublin, OH (US)

(73) Assignee: Michigan Biotechnology Institute, Lansing, MI (US)

( * ) Notice: Subject to any disclaimer, the term of this patent is extended or adjusted under 35 U.S.C. 154(b) by 361 days.

(21) Appl. No.: 12/791,703

(22) Filed: Jun. 1, 2010

(65) Prior Publication Data
US 2011/0290114 A1    Dec. 1, 2011

(51) Int. Cl.
*B01D 53/02* (2006.01)
(52) U.S. Cl. .................. 95/90; 95/128; 95/139; 95/148; 435/183; 435/277; 127/37
(58) Field of Classification Search ............. 95/90, 128, 95/139, 148; 435/183, 277; 127/37
See application file for complete search history.

(56) References Cited

U.S. PATENT DOCUMENTS

| | | | |
|---|---|---|---|
| 2,017,779 A * | 10/1935 | Vosburgh | 95/139 |
| 2,548,192 A * | 4/1951 | Berg | 95/111 |
| 3,306,006 A * | 2/1967 | Urban | 95/97 |
| 3,920,419 A | 11/1975 | Schroeder et al. | |
| 4,153,435 A | 5/1979 | Fischer | |
| 4,581,044 A | 4/1986 | Uno et al. | |
| 4,594,131 A | 6/1986 | Maier | |
| 4,986,835 A * | 1/1991 | Uno et al. | 95/99 |
| 4,995,888 A | 2/1991 | Beaupre et al. | |
| 5,025,635 A | 6/1991 | Rockenfeller et al. | |
| 5,114,694 A | 5/1992 | Grotz, Jr. | |
| 5,171,592 A | 12/1992 | Holtzapple et al. | |
| 5,660,603 A | 8/1997 | Elliot et al. | |
| 6,027,552 A | 2/2000 | Ruck et al. | |
| 6,425,939 B1 * | 7/2002 | Moreau et al. | 95/117 |
| 6,524,848 B2 | 2/2003 | McNelly | |
| 6,585,807 B2 | 7/2003 | Umino et al. | |
| 6,872,296 B2 | 3/2005 | Kim | |
| 6,893,484 B2 | 5/2005 | Thomas | |
| 7,250,074 B2 * | 7/2007 | Tonkovich et al. | 95/130 |
| 2005/0064577 A1 * | 3/2005 | Berzin | 435/266 |
| 2007/0113736 A1 * | 5/2007 | Bandosz | 95/136 |

(Continued)

FOREIGN PATENT DOCUMENTS

| WO | WO 2005/091418 A2 | 9/2005 |
|---|---|---|
| WO | WO 2006/055362 A1 | 5/2006 |

OTHER PUBLICATIONS

Fulks, G. et al., A review of Solid Materials as Alternative Ammonia Sources for Lean NOx Reduction with SCR, SAE International Report 2009-01-0907 (2009).

(Continued)

*Primary Examiner* — Duane Smith
*Assistant Examiner* — Christopher P Jones
(74) *Attorney, Agent, or Firm* — Dickinson Wright, PLLC

(57) ABSTRACT

This invention provides methods for separating gas components from a gas stream. The methods are particularly advantageous in that an environmentally friendly biomass absorbent is used to assist in the separation process. The invention is particularly suited to separate water soluble gas components from a gas stream. The water soluble gas components can be used to condition the biomass for additional use, such as a conditioned feed for a biofuel. In general, the conditioned biomass will have increased enzyme digestibility, making the conditioned biomass highly suitable as feedstock for biofuel production.

13 Claims, 4 Drawing Sheets

U.S. PATENT DOCUMENTS

| | | | |
|---|---|---|---|
| 2008/0087165 A1* | 4/2008 | Wright et al. | 95/51 |
| 2008/0115415 A1* | 5/2008 | Agrawal et al. | 48/101 |
| 2008/0264254 A1 | 10/2008 | Song et al. | |
| 2009/0049748 A1* | 2/2009 | Day et al. | 48/77 |
| 2009/0087898 A1* | 4/2009 | Haase et al. | 435/262.5 |
| 2009/0099079 A1* | 4/2009 | Emalfarb et al. | 514/12 |
| 2009/0123361 A1 | 5/2009 | Johannessen et al. | |
| 2009/0221042 A1 | 9/2009 | Dale et al. | |
| 2009/0230040 A1* | 9/2009 | Limcaco | 210/151 |
| 2009/0313976 A1 | 12/2009 | Johannessen et al. | |

OTHER PUBLICATIONS

Kawasaki, N. et al., Deodorization of Ammonia by Coffee Grounds, Journal of Oleo Science, 55(1):31-35 (2006).

Selig, M. et al., Enzymatic Saccharification of Lignocellulosic Biomass, National Renewal Energy Laboratory Technical Report TP-510-42629, 1-5 (Mar. 2008).

PCT/US2011/038524, PCT International Search Report, Form PCT/ISA/210, dated Feb. 9, 2012, 3 pgs.

PCT/US2011/038524, PCT Written Opinion of the International Searching Authority, Form PCT/ISA/237, dated Feb. 9, 2012, 5 pgs.

Sheridan, B.A., et al. "Assessment of the influence of media particle size on the biofiltration of odorous exhaust ventilation air from a piggery facility", Bioresource Technology, 2002, No. 84, pp. 129-143.

Deshusses, Marc A. "Biological waste air treatment in biofilters", Current Opinion in Biotechnology, 1997, No. 8, pp. 335-339.

* cited by examiner

METHOD OF SEPARATING COMPONENTS FROM A GAS STREAM

FIELD OF THE INVENTION

This application relates to methods of separating at least one gas component from a gas stream using a biomass material. In particular, this invention relates to methods of separating at least one gas component from a gas stream using the biomass material, and increasing enzyme digestibility of the biomass.

BACKGROUND OF THE INVENTION

Separation of gas mixtures has been achieved using a variety of techniques. Examples of such techniques include distillation, membrane separation, gas-liquid absorption, and gas-solid adsorption. These techniques can be based on one or more of chemical and physical differences between the components being separated.

In distillation, the components of a gas mixture are separated by exploiting differences in the bubble- and dew-point temperatures of the components. Distillation columns are designed to provide intimate contacting of vapor and condensed liquid streams over a series of plates or packed sections, so that a temperature difference between the bottom and top of the column yields streams with different compositions. Distillation equipment is capital-intensive, and the operation of distillation columns is notoriously complex and difficult to automate, so that skilled operators are generally required.

Membranes have been used to separate gases from gases and gases from liquids. Gas separations can use either porous or nonporous polymeric membranes. In porous membrane separation, pore diameter is typically smaller than the mean free path of the gas molecules. In nonporous membranes, separation is generally based on differences in solubility and diffusivity in the polymer. Gas-liquid separation membranes are generally based on gas permeability or diffusion or on gas-permeable pores providing separation by capillary force. U.S. Pat. No. 4,995,888 shows one example of gas separation from a liquid using a membrane in which the separation is based on absorption. Acid and base gases can be separated.

Soluble vapors can be separated from mixtures with inert gases by absorption into an appropriate liquid solvent. Gas-liquid absorption processes can employ packed beds of inert solid particles, with the liquid solvent gravity-flowing downward over the inert solid particle surfaces. The mixture of inert gas with soluble vapor flows upward through the bed, contacting the liquid in counter-current flow. Absorption of the soluble vapor into the liquid can provide a pure stream of inert gas exiting the top of the bed, but the soluble component is recovered as a solution in the liquid. This liquid solution must be subsequently separated if the soluble vapor and liquid solvents are to be re-used as pure components. In operation of a gas-liquid absorption bed, the velocities of both the liquid and gas streams are controlled to prevent either dry or flooded conditions in the bed.

U.S. Pat. No. 3,920,419 provides and example of a method of removing ammonia from an ammonia containing liquor using a packed column. The ammonia-containing liquor is fed to the top of the packed column, while monitoring the pH of the feed liquor. Caustic is added in controlled amounts to the feed liquor prior to introduction into the column to maintain a minimum pH of 10.5. A gaseous stripping medium is flowed in a countercurrent manner through the column at the minimum temperature of about 140° F., while regulating the flow of the feed liquor to the column. The flow of the stripping medium is controlled so that at least 99% of the ammonia is removed from the liquor.

Gas components of a gas mixture can also be separated using solid adsorbent materials. Since adsorption is a surface phenomenon, adsorption capacity increases with the specific surface area of the solid adsorbent, so materials with very high specific surface areas are commonly used. Some examples include adsorption of oxygen from air using activated carbon, adsorption of ammonia from nitrogen using metal salts (Christensen et al 2005, WO 2005/091418; Johannesen et al 2009, U.S. patent Pub. Nos. 2009/0123361 and 2009/0313976; Fulks et al 2009, SAE International Report 2009-01-0907), ammonia adsorption on dried coffee grounds and activated carbon for air deodorization (Kawasaki et al 2006, J. Oleo Sci. vol 55., no. 1, pp 31-35), and hydrogen purification by adsorption of impurities from reformate gas using zeolite molecular sieves.

Commercial gas-solid adsorption processes often employ packed beds of solid adsorbent particles operated first at high pressure to selectively remove one component of a gas mixture, followed by desorption of the bed at low pressure to recover the adsorbed species and regenerate the adsorbent. These cyclic operations are known as Pressure-Swing Adsorption (PSA) processes. Solid adsorbents may also be desorbed and regenerated by heating, known as Temperature-Swing Adsorption (TSA). The adsorbents used in gas-solid separations are often expensive, and their performance can be degraded by irreversible sorption of moisture, oils, or other contaminants. Adsorption of ammonia from inert gases using metal salts is limited by the rate of diffusion of ammonia into the bulk salt particles, and therefore does not allow for rapid adsorption and separation of ammonia from the inert gas.

Ammonia has been used to treat biomass material. In the treatment process, after contacting with biomass, the ammonia is separated, recovered and recycled, typically by what has been referred to as an Ammonia Fiber Explosion (AFEX) process.

Holtzapple et al., U.S. Pat. No. 5,171,592, discloses an AFEX process in which liquid ammonia is contacted with biomass material in a reactor. The ammonia vaporizes in the reactor causing the biomass to cool. The ammonia also causes the biomass to swell and decrystallize. When decrystallization is complete, the reactor is opened, causing the ammonia to flash off of the biomass. The flashed ammonia is recovered and recycled to contact fresh biomass.

Rajagopalan et al., WO 2006/055362, also discloses an AFEX process in which liquid ammonia is contacted with biomass material in a reactor. The reactor does not allow vaporization of the ammonia. However, when the biomass has been in contact with the liquid ammonia for a time sufficient to treat the biomass, the reactor is opened, causing the ammonia to flash off of the biomass. The flashed ammonia is recovered and recycled to contact fresh biomass.

Dale et al., U.S. patent Pub. No. 2009/0221042, discloses a process for treating biomass to render structural carbohydrates more accessible and/or digestible using concentrated ammonium hydroxide. The process uses steam to strip ammonia from biomass for recycling. The process yields of monosaccharides from the structural carbohydrates are considered to be good as indicated by enzymatic hydrolysis under standardized conditions ("Enzymatic saccharification of lignocellulosic biomass," National Renewable Energy Laboratory Technical Report TP-510-42629, March 2008).

More efficient methods of separating gas components are desired. Particularly desired are methods that are less energy- and capital-intensive relative to known processes.

Also of interest would be methods that allow for use of biological or biomass materials in the separation process. Such materials are considered renewable and, therefore, of environmental benefit. The ability to use these materials for other downstream uses would also be of benefit.

SUMMARY OF THE INVENTION

This invention provides methods for separating gas components in a highly efficient manner. The methods are of particular benefit in that they are less energy- and capital-intensive than many processes currently available.

The invention is also of environmental benefit in that it provides a use for renewable materials such as biomass. The biomass serves as the separation means in this invention, and the biomass can ultimately be used to provide chemical products of value.

According to one aspect of the invention, there is provided a method of separating at least one gas component from a gas stream. The method includes a step of flowing a feed gas stream to contact a biomass material within a vessel, with the feed gas stream comprised of at least a first gas component and a second gas component. At least a portion of the first gas component is separated from the feed gas stream that contacts the biomass material as the second gas component of the feed gas stream flows through the vessel. An effluent gas stream that contains a reduced concentration of the first gas component relative to that in the feed gas stream is collected from the vessel.

The first gas component of the feed gas stream is preferably a water soluble gas. The water soluble gas preferably has a Henry's Law constant ($K_H$) at 25° C. of at least 0.002 mole/L-atm.

The second gas component of the feed gas stream is preferably a water insoluble gas. The water insoluble gas preferably has a Henry's Law constant ($K_H$) at 25° C. of less than 0.002 mole/L-atm.

The pressure of the vessel is at least atmospheric. Preferably, the vessel is maintained at a pressure that is greater than the saturation pressure of water present in the vessel.

The biomass material is a moist material. Preferably, the biomass material is comprised of at least 10 wt % water, based on total weight of the biomass.

The first gas component and the second gas component are preferably mixed together to form the feed gas stream prior to contacting the biomass material.

In one embodiment of the invention, the first gas component is retained within the vessel until the biomass material is increased in enzyme digestibility.

According to another aspect of the invention, there is provided a method of separating gas components. A feed gas stream comprised of at least a first gas component and a second gas component is sent to a vessel to contact a biomass material within the vessel. Preferably, the biomass material contains at least 10 wt % water, based on total weight of the biomass.

At least a portion of the first gas component is separated from the second gas component as the feed gas stream is flowed through the vessel. An effluent gas stream that contains a reduced concentration of the first gas component relative to that in the feed gas stream is collected from the vessel.

According to another aspect of the invention there is provided a method of removing at least one gas component of a gas stream. A feed gas stream comprised of at least a first gas component and a second gas component is sent to a vessel to contact a biomass material in the vessel, and at least a portion of the first gas component is retained within the vessel as the second gas component of the feed gas stream is flowed through the vessel.

In the invention, an effluent stream is collected from the vessel. This effluent stream is depleted in concentration of the at least first gas component relative to the feed gas stream. A purge gas stream different in composition from that of the feed gas stream can be sent to the vessel to remove at least a portion of the first gas component retained within the vessel.

DETAILED DESCRIPTION OF THE INVENTION

Introduction

Figure 1A:
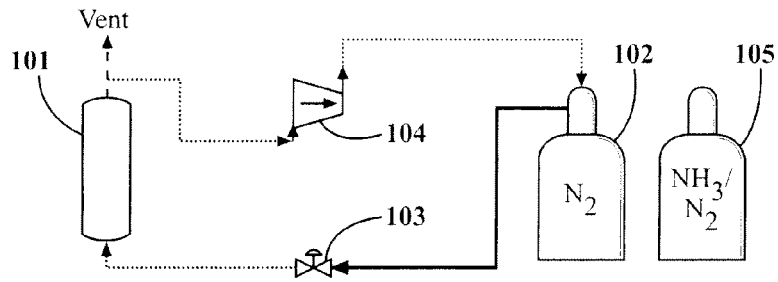
FIG. 1 is a flow diagram of one embodiment of the invention that incorporates the use of a single vessel.

This invention provides methods for separating gas components from a gas stream. The methods are particularly advantageous in that an environmentally friendly biomass absorbent is used to assist in the separation process.

The invention is particularly suited to separate water soluble components from a gas stream. In preferred embodiments, the water soluble components are acid or base gases. These gases can be used to condition the biomass for additional use, such as a conditioned feed for a biofuel. In general, the conditioned biomass will have increased enzyme digestibility, making the conditioned biomass highly suitable as feedstock for biofuel production.

Feed Gas Stream

The feed gas stream contains the gas component that is to be separated and/or recovered. This feed gas stream is a gas stream that is sent to a vessel containing biomass that is used to separate the desired gas component.

The feed gas stream is comprised of at least a first gas component and a second gas component. There may be more than one gas component (i.e., compound) that is present in the feed gas stream. Preferably, at least one gas component is water soluble. It is also preferable that at least one gas component is water insoluble.

In one embodiment, the at least first and second gas components are mixed together to form the feed gas stream, and the feed gas stream is sent to the vessel containing the biomass. In another, the at least first and second gas components are sent to the vessel containing the biomass by way of separate conduits and mixed together to form the feed gas stream in the vessel prior to contacting the biomass.

In one embodiment of the invention, at least one gas component, i.e., the first gas component or component that is desired to be separated from the gas stream, is water soluble. Water solubility of a gas is preferably determined according to this invention by Henry's law. According to Henry's law, at a constant temperature, the amount of a given gas dissolved in a given type and volume of liquid is directly proportional to the partial pressure of that gas in equilibrium with that liquid.

Henry's law can be put into mathematical terms (at constant temperature) as $c=k_H p$, where p is the partial pressure of the solute in the gas above the solvent, c is the molar concentration of the solute in the solvent, and $k_H$ is an equilibrium constant with the dimensions of molar concentration divided by pressure. The constant, known as the Henry's law constant, depends on the solute, the solvent and the temperature. In this invention, the solute is the gas component that is desired to be separated and/or recovered from a gas mixture, and the solvent is preferably considered water. For example, the water that is present as moisture in the biomass is preferably considered the solvent. The value of Henry's law constant according to this invention is provided at 25° C.

Any gas component that is desired to be separated and/or recovered from a gas stream according to this invention is preferably a water soluble gas having a Henry's law constant ($k_H$) at 25° C. of at least 0.002 mole/L-atm. Preferably, the soluble gas component has a Henry's law constant ($k_H$) at 25° C. of at least 0.02 mole/L-atm, more preferably at least 0.1 mole/L-atm, and most preferably at least 1 mole/L-atm.

Examples of water soluble gas components include, but are not limited to, nitric acid, hydrogen chloride, hydrogen peroxide, formaldehyde, acetic acid, ammonia, nitrous acid, sulfur dioxide, hydrogen sulfide, carbon dioxide, carbon disulfide, hydrogen cyanide, carbonyl sulfide, methyl mercaptan and ethyl mercaptan. If more than one water soluble gas component is a gas stream, then the water soluble components can be separated and/or recovered together.

Any gas component that is not desired to be separated and/or recovered from a gas stream according to this invention is preferably a water insoluble gas having a Henry's law constant ($k_H$) at 25° C. less than 0.002 mole/L-atm. Preferably, the insoluble gas component has a Henry's law constant ($k_H$) at 25° C. of not greater than 0.01 mole/L-atm, more preferably not greater than 0.005 mole/L-atm, and most preferably not greater than 0.002 mole/L-atm.

Examples of water insoluble gas components include, but are not limited to, methane, oxygen, carbon monoxide, nitrogen, hydrogen, helium, neon and argon. More than one water insoluble gas can be included in the gas feed stream. In general, such gases will pass or flow through a vessel containing biomass, without any significant retention of those gases in the vessel.

In one embodiment, the water soluble gas is a base gas. A base gas is a gas that when dissolved in water, increases the pH of the water. Increase in pH can be measured directly or indirectly. In one embodiment, increase in pH is measured through the use of an acid trap, such as a citric acid trap. A base gas that is soluble in water can be passed through an aqueous citric acid solution and the pH monitored. As the base gas is absorbed into the aqueous solution, the pH will increase. Examples of water soluble base gases include, but are not limited to, ammonia, alkyl amines and pyridine.

In another embodiment, the water soluble gas is an acid gas. An acid gas is a gas that when dissolved in water, decreases the pH of the water. Decrease in pH can be measured directly or indirectly. In one embodiment, decrease in pH is measured through the use of a base trap, such as a sodium hydroxide trap. An acid gas that is soluble in water can be passed through an aqueous sodium hydroxide acid solution and the pH monitored. As the acid gas is absorbed into the aqueous solution, the pH will decrease. Examples of water soluble acid gases include, but are not limited to, nitric acid, hydrogen chloride, hydrogen peroxide, formaldehyde, acetic acid, nitrous acid, sulfur dioxide, hydrogen sulfide, carbon dioxide, carbon disulfide, hydrogen cyanide, carbonyl sulfide, methyl mercaptan and ethyl mercaptan.

In one embodiment, the feed gas stream has a water soluble gas concentration of at least 1 mass %, based on total weight of the feed gas stream. In another, the feed gas stream has a water soluble gas concentration of at least 5 mass %, or at least 10 mass % or at least 20 mass %, based on total weight of the feed gas stream. The water soluble gas concentration includes all water soluble gases present in the feed gas stream. One or more water soluble gases can be present.

In another embodiment, the feed gas stream has a water insoluble gas concentration of at least 10 mass %, based on total weight of the feed gas stream. In another, the feed gas stream has a water insoluble gas concentration of at least 20 mass %, or at least 30 mass %, or at least 40 mass %, or at least 50 mass %, based on total weight of the feed gas stream. The water insoluble gas concentration includes all water insoluble gases present in the feed gas stream. One or more water insoluble gases can be present.

The at least one component that is also desired to be separated from the feed gas stream has a higher vapor pressure than water. Preferably, the vapor pressure of the at least one gas component is at least twice that of water, more preferably at least 5 times that of water, and most preferably at least 10 times that of water.

Biomass

The term biomass, for the purposes of this invention, is considered any material not derived from fossil resources and comprising carbon, hydrogen, and oxygen. Examples of biomass include, but are not limited to, plant and plant-derived material, vegetation, agricultural waste, forestry waste, wood waste, paper waste, animal-derived waste, poultry-derived waste, municipal solid waste, cellulose, and carbohydrates or derivates thereof.

Additional examples of biomass include, but are not limited to, timber harvesting residues, softwood chips, hardwood chips, tree branches, tree stumps, leaves, bark, sawdust, off-spec paper pulp, food waste, corn, corn cob, corn stover, wheat straw, rice straw, oat straw, oat hulls, sugarcane bagasse, citrus peel, switchgrass, miscanthus, tobacco, animal manure, municipal garbage, municipal sewage, commercial waste, grape pumice, almond shells, pecan shells, coconut shells, coffee grounds, grass pellets, hay pellets, wood pellets, cardboard, paper, and cloth.

The biomass preferably contains water in an amount that allows for absorption of at least one water soluble gas component. Preferably, the biomass contains at least 10 wt % water, based on total weight of the biomass. In other embodiments, the biomass contains at least 20 wt % or 30 wt % water, based on total weight of the biomass. In a particular embodiment, the biomass material is comprised of from 15 wt % to 70 wt % water, or from 20 wt % to 60 wt % water, based on total weight of the biomass.

The biomass can be processed prior to insertion into the vessel in which the separation of the desired gas component is carried out. For example, the biomass can be ground in a mill until a desired particle size is achieved. The preferred particle size is dependent on the vessel dimensions, biomass, and process conditions. In one embodiment, the particle size of the biomass to be used in the separation vessel is sufficiently ground to pass through a 1 mm screen, in another through a 10 mm screen, in another through a 20 mm screen, and in another through a 30 mm screen.

Process Conditions

The process of this invention is preferably carried out at temperatures and pressures at which the at least one water soluble component of the feed gas stream remains predominantly in the gas state as the feed stream enters the vessel containing the biomass. The vessel in which the gas component that is desired to be separated from the feed gas stream is preferably a closed vessel in that it is not open to the atmosphere as the process is carried out.

Temperature and pressure within the vessel in which the process is carried out is preferably maintained below the boiling point of water. Such a vessel is, therefore, preferably maintained at a pressure greater than the saturation vapor pressure of water within the vessel. More preferably, the actual pressure will be at least 25% greater, or at least 50% greater, or at least 100% greater, than the saturation vapor pressure of water within the vessel.

According to this invention, it is particularly preferred to carry out the process at a temperature sufficiently low so as to maximize separation of the desired gas component from the gas feed stream. At lower temperatures, the gas component is more effectively absorbed by water within the vessel, such as by the water component that can be included as a part of the biomass. The temperature, however, should not be so low as to condense a significant portion of the gas component that is to be separated at the particular operating pressure.

In one embodiment of the invention, the process is carried out at such that the vessel containing the biomass is within a range of from 25° C. to 200° C. Preferably, the process is carried out such that the temperature of the vessel containing the biomass is within a range of from 30° C. to 180° C., more preferably from 50° C. to 150° C.

It is also preferred to carry out the process of this invention at a pressure sufficiently high to maximize separation of the desired gas component from the feed stream. Preferably, pressure is high enough to favor absorption of the desired gas component by water, such as by the water component that is included as a part of the biomass.

In another embodiment of the invention, the process is carried out such that the pressure of the vessel containing the biomass is within a range of from 20 psia (137.9 kPaa) to 1000 psia (6895 kPaa). Preferably, the process is carried out such that the pressure of the vessel containing the biomass is within a range of from 40 psia (275.8 kPaa) to 800 psia (5516 kPaa), more preferably from 60 psia (413.7 kPaa) to 500 psia (3447 kPaa).

In one embodiment, the process is carried out by flowing a feed gas stream comprised of a mixture of gas components, e.g., at least a first gas component and a second gas component, to a vessel containing biomass material. At least a portion of the first gas component is separated from the feed gas stream as the feed gas stream flows through the vessel. To minimize dispersive effects, flow rate of the feed gas to the vessel is preferably controlled at a Gas Hourly Space Velocity (GHSV) of less than 500 $hr^{-1}$, and most preferably less than 200 $hr^{-1}$.

Since at least a first gas component is separated from the feed gas stream as it flows through the vessel, an effluent gas stream can be recovered from the vessel in which the effluent gas stream contains a reduced concentration of the first gas component relative to that contained in the feed gas stream. Preferably, the effluent gas stream contains less than 50%, more preferably less than 30%, and most preferably less than 10% of the first gas component relative to that in the feed gas stream.

In one embodiment of the invention, the feed gas stream containing the at least first gas component is flowed through the vessel containing the biomass material until removal of the first gas component in the vessel becomes substantially reduced or until a significant amount of the at least first gas component is found to be present in the effluent stream. The concentration of the at least first gas component can be measured using any suitable means, including but not limited to, gas chromatography, electrochemical detection, photoionization detection, photoacoustic detection, and acid/base back-titration of a trap solution.

In one embodiment of the invention, the process is carried out such that the biomass material is present as a fixed bed of particles within the vessel. For purposes of this invention, a fixed bed of particles is considered to be a mass of particles in which each particle has a position that is fixed relative to one another. Such a bed can be moving or static. In moving, fixed bed systems, movement is preferably carried out at substantially plug flow. Such flow can be accomplished using any appropriate movement means that minimizes back-mixing. Examples of such movement means include, but are not limited to, a screw conveyor, belt conveyor, tubular drag chain conveyor and pneumatic conveyor. In moving beds, the particles can be conveyed through the vessel in counter-current or co-current direction relative to the direction of feed gas flow.

Separation of at least a first gas component from the feed gas stream can be carried out as a batch process, in which concentrations of the at least first gas component in the gas stream that are absorbed in the biomass particles change with time and with the positions of the particles in the bed. As the feed gas stream containing the at least first gas component is flowed through the vessel containing the fixed bed of biomass particles, absorption of the at least first component by the biomass through the bed results in reduction in the concentration of the at least first component in the gas stream along downstream portions of the bed, i.e., toward the outlet of the vessel. A concentration profile is established across the bed, with a higher concentration of the at least first component at the influent end of the bed, and a lower concentration at the effluent end of the bed and in the effluent gas flowing from the bed. With continuing flow of the feed gas stream into the fixed bed, this concentration profile moves toward the effluent end of the bed, until the concentration of the at least first gas component in the effluent gas stream becomes greater than a predetermined or desirable quantity.

The point at which the concentration of the at least first gas component in the effluent gas stream becomes greater than the predetermined or desirable quantity is referred to as breakthrough of the fixed bed. Prior to breakthrough, the effluent gas can be collected and stored for subsequent re-use, as it contains an acceptably low concentration of the at least first gas component. As flow of the feed gas stream into or across the bed is continued after breakthrough, the concentration of the at least first gas component in the effluent gas stream increases, until the concentrations in the feed and effluent streams are substantially the same, at which point the bed is considered saturated with the at least first gas component.

At a breakthrough point when the concentration of the at least one gas component that is desired to be separated from the gas feed stream gets to an undesirably high concentration in the effluent stream, collection of the effluent stream depleted in concentration of the at least first gas component is preferably ceased. In one embodiment, collection is ceased at a point at which the effluent gas stream contains at least 5 mass % of the first gas component, based on total mass of the effluent gas stream. Preferably, collection of the effluent stream is ceased at a point at which the effluent gas stream contains at least 1 mass %, more preferably at least 0.1 mass %, of the first gas component, based on total mass of the effluent gas stream.

In one embodiment of the invention, the at least one gas component that is desired to be separated from the gas feed stream is a base or acid gas. In such case, at least a portion of the effluent stream, e.g., a slipstream, can be sent to a vessel or trap and the pH of liquid in the vessel or trap monitored. An increase in base gas concentration can be indicated by an increase in pH at the vessel or trap, and an increase in acid gas concentration can be indicated by a decrease in pH at the vessel or trap. At such point, collection of the effluent stream depleted in concentration of the at least first gas component is preferably ceased.

In another embodiment, absorption of the at least one gas component that is desired to be separated from the gas feed stream causes an increase in temperature of biomass as it contacts water contained in the biomass material. This increase in temperature can also be used to determine when to cease collection of the effluent stream depleted in concentration of the at least one gas component. For example, as a feed gas stream is flowed to a vessel containing the biomass material, the biomass material will heat in proportion to contact with water contained in the biomass material. In general, the at least first gas component will initially be absorbed at the influent end of the vessel, thereby causing an increase in temperature of the biomass material at the influent end. As the feed gas stream continues to flow through the vessel, the at least first gas component will be absorbed along the flow path, generally causing a corresponding increase in temperature of the biomass material. Once the at least first gas component has been essentially saturated within the biomass material, there will be little if any further separation or absorption. In one way, this can be indicated by an increase in temperature of the biomass material at the effluent end of the vessel. At a point at which temperature at an effluent end of the vessel is increased, the collection of the effluent stream depleted in concentration of the at least first gas component is ceased.

In one embodiment, collection of the effluent stream depleted in concentration of the at least first gas component is ceased at a point at which the effluent gas (i.e., gas leaving the vessel) is at a temperature not less than 5° C. below that of the influent gas (i.e., gas sent to the vessel). Preferably, collection of the effluent stream depleted in concentration of the at least first gas component is ceased at a point at which the effluent gas is at a temperature not less than that of the influent gas (i.e., gas sent to the vessel). More preferably, collection is ceased at a point at which the effluent gas is at a temperature greater than that of the influent gas.

The at least one gas component that has been separated from the feed gas stream can be recovered from the vessel containing the biomass material by sending a purge gas stream different in composition from that of the feed gas stream to the vessel to remove at least a portion of the first gas stream contained in the vessel. The purge gas stream is preferably comprised of water insoluble gas. Preferably, the purge gas stream is comprised of at least 90 mass %, more preferably at least 95 mass %, and most preferably at least 98 mass % water insoluble gas, based on total mass of the purge gas stream. It is understood that the purge gas can be comprised of one or more water insoluble gases, i.e., a mixture of water insoluble gases. In the case of a mixture of water insoluble gases, the preferred ranges should be understood to mean the total content of the mixture of water insoluble gases. In one embodiment, the purge gas may be a portion of the effluent gas that was collected prior to the breakthrough point.

The flow of purge gas can be co-current or countercurrent relative to the direction of flow of the feed gas stream. In one embodiment, the purge gas stream is sent to the vessel containing the biomass material in a direction countercurrent relative to that of the flow of the feed gas stream. In another, the purge gas stream is sent to the vessel containing the biomass material in a direction co-current relative to that of the flow of the feed gas stream. The at least one gas component can then be recovered as the purge gas is flowed to the vessel containing the biomass material.

Vessel

The at least one gas component that is desired to be separated and/or recovered from a feed gas stream according to the invention is separated from the gas stream in a vessel that is preferably closed, i.e., not open to the atmosphere. Any vessel suitable for containing biomass material and through which the feed gas stream can be passed or flowed can be used.

Preferably, the vessel is a tube or hollow cylinder. In a particular embodiment, the vessel is a tube or hollow cylinder having ports located near its axis at either end to permit flow of influent and effluent gas streams.

In one embodiment of the invention, the vessel has an internal axial length greater than its internal diameter to enhance separation. In a more preferred embodiment the vessel has an internal axial length at least eight times greater than its internal diameter, still more preferably at least ten times greater than its internal diameter, and most preferably at least twelve times greater than its internal diameter.

Biomass material can be retained as a static or moving bed within the vessel. In the form of a static bed, the biomass can be retained by means of support mesh or screens fitted at the influent and effluent ends of the vessel. Mesh or screens with openings smaller than the biomass particles, preferably at least five times smaller, and most preferably at least ten times smaller, are used. At each end of the vessel, a plenum is preferably provided to allow for even gas flow distribution throughout the bed of biomass particles.

The vessel can be arranged as part of a batch or continuous process system. There can be only one vessel, although more than one vessel can be used. In embodiments that incorporate more than one vessel in which biomass material is contained, the vessels can be arranged in parallel or series.

In one embodiment, there is provided a separation system that includes at least two vessels in series. Preferably, the system has from 3 to 10 vessels in series, and in one embodiment the system has from 3 to 5 vessels in series.

The series arrangement of vessels is particularly advantageous in that it allows for internal circulation or recycle of insoluble gas, thereby reducing the amount of insoluble gas needed to displace or recover soluble gas after the soluble gas has been absorbed into the biomass material. Such a system acts in essence like a pressure swing absorber in which one vessel can be used to separate and absorb water soluble gas, while another vessel is being purged of water soluble gas for recovery of the gas. This also allows a vessel to be isolated after being purged of the water soluble gas, so that the biomass material can be removed and replaced from that vessel without having to shut down the entire system.

Further Processing of Biomass

In certain embodiments of the invention, the biomass material can be further processed. For example, the biomass material can be removed following purging of the water soluble gas from the vessel and then be used to produce chemical derivates such as to make ethanol or other compositions useful as transportation fuel or fuel components. In such an example, the biomass material can be fermented to produce the desired fuel components.

In a preferred embodiment of the invention, the at least one separated gas component is retained within the vessel containing the biomass material to increase enzyme digestibility of the biomass. More preferably, the at least one gas component is retained in the vessel to increase enzyme digestibility, then the retained gas component collected or recovered.

Enzyme digestibility refers to the ability of the biomass material to be converted into its constituent sugar components by hydrolytic enzymes. According to this invention, enzyme digestibility is measured using a standard laboratory protocol (See, e.g., "Enzymatic saccharification of lignocellulosic biomass," National Renewable Energy Laboratory Technical Report TP-510-42629, March 2008.).

For the purposes of this invention, enzyme digestibility is the rate at which a biomass material may be digested to one or more of glucose and xylose using cellulase or xylase enzymes. The quantitative effect of contact or treatment of the biomass material with the at least first gas component with regard to the enzyme digestibility of the biomass material can be measured by adding 0.15 grams dry mass of biomass sample that has been contacted or treated with the at least first gas component to a glass scintillation vial, and the same dry mass of biomass that has not been contacted or treated to a separate vial. Preferably, duplicate vials of both biomass samples are prepared.

To each vial is then added 5.0 milliliters of 0.1 molar pH 4.8 sodium citrate buffer, and a quantity of cellulase enzyme solution equal to 1.5 Filter Paper Units (FPU) of activity. An equal quantity of xylase enzyme can also be added to each vial.

The total volume in each vial is then diluted to 10.0 milliliters by adding distilled water. The vials are then sealed and incubated at 50±1° C., with sufficient agitation to keep the solids suspended, for 48 hours. Conditions during the incubation period, including temperature and pH, can be adjusted as necessary to suit the particular enzymes used in digestion. After incubation, a liquid aliquot is drawn from each vial and filtered through a 0.45-micron filter, and the filtrate is then analyzed to determine the concentration of glucose, xylose, or both using HPLC or any other suitable quantitative technique.

Increased enzyme digestibility of biomass can then be calculated as $X_{cell}=100*[(C_{Glu})_{abs}/(C_{Glu})-1]$, where $X_{cell}$ is the percent increase in enzyme or cellulase digestibility, $(C_{Glu})_{abs}$ the concentration of glucose in the filtrate from the biomass that has been contacted or treated with the at least first gas component, and $(C_{Glu})$ is the concentration of glucose in the filtrate from the biomass that has not been contacted or treated with the at least first gas components.

A similar calculation can be performed for increased enzyme digestibility based on the concentrations of xylose in the filtrate aliquots. In such a case, $X_{cell}=100*[(C_{Xyl})_{abs}/(C_{Xyl})-1]$, where $X_{cell}$ is the percent increase in enzyme or xylase digestibility, $(C_{Xyl})_{abs}$ is the concentration of xylose in the filtrate from the biomass that has been contacted or treated with the at least first gas component, and $(C_{Xyl})$ is the concentration of xylose in the filtrate from the biomass that has not been contacted or treated with the at least first gas components. Preferably, contact or treatment of the biomass material with the at least one water soluble gas component increases enzyme digestibility by at least 5%, more preferably by at least 50%, and most preferably by at least 100%. This increase can be measured by one or more of an increase in cellulase and xylase digestibility as defined by cell.

In one embodiment of the invention, the flow of the at least first gas component (i.e., any and all soluble gases sent to the vessel containing the biomass material) is ceased and the at least first gas component remains in contact with the biomass material to increase enzyme digestibility by at least 10% relative to that initially supplied to the vessel. Preferably, the flow of the at least first gas component is ceased and the at least first gas component remains in contact with the biomass material to increase enzyme digestibility by at least 20%, more preferably at least 30%, and most preferably at least 40%, relative to that initially supplied to the vessel.

EXAMPLES

Example 1

One embodiment of the invention is shown in FIGS. 1A-1E, which uses a single vessel for gas component separation. As shown in FIG. 1A, a vessel containing biomass material 101 is swept with a water insoluble gas (e.g., nitrogen) from a tank 102 to eliminate air to vent, then the vessel is pressurized. Pressure is controlled with a pressure regulator valve 103, with recirculation provided by compressor 104.

Figure 1B:
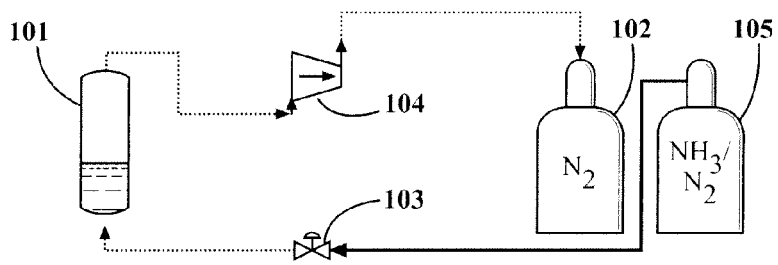

In FIG. 1B, a gas feed stream comprised of a mix of a first gas component (e.g., ammonia) and a second gas component (e.g., nitrogen) is sent from a tank 105 to the vessel 101. In the vessel 101, the first gas component is separated from the second gas component by absorption. As absorption is taking place, the second gas component continues to flow through the vessel 101. The second gas component leaves the vessel 101 and is sent to the compressor 104, and to the tank 102.

Figure 1C:
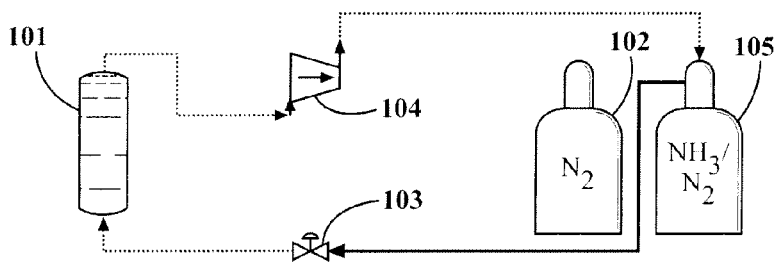

In FIG. 1C, breakthrough of the at least first gas component is detected by the temperature increase at the effluent end of the vessel. Return flow of the mix of the first and second gas components from the effluent end is directed to tank 105. The flow is then recirculated to the bed 101 to ensure maximum absorption of the first gas component in the biomass material. Flow to the vessel 101 is then stopped. The first gas component is allowed to remain in contact with the biomass material to treat the biomass material, such as for example to achieve an increase in enzyme digestibility.

Figure 1D:
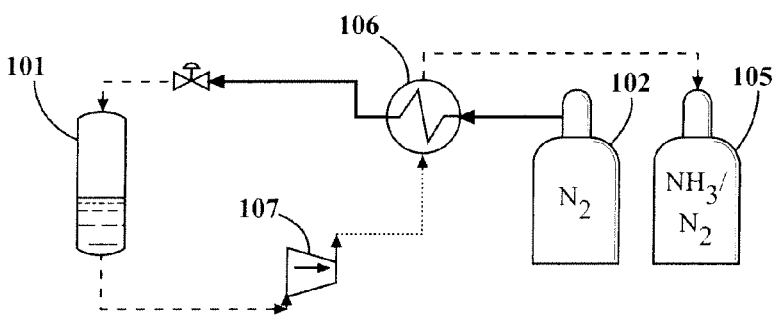

In FIG. 1D, a gas stream from tank 102 is sent to the effluent end of the vessel 101 through an optional heat exchanger 106. This flow of second gas component is used to desorb or purge the first gas component from vessel 101 at a lower pressure than was used for absorption of the first gas component in FIGS. 1B and 1C, sending a mixture of the first gas component with the second gas component to tank 105 by way of a compressor 107 and optional heat exchanger 106. Although the flow of the purge gas stream in this embodiment, is shown as countercurrent to that of the feed gas stream, the flow could also be in a direction co-current relative to that of the direction of feed gas flow.

Figure 1E:
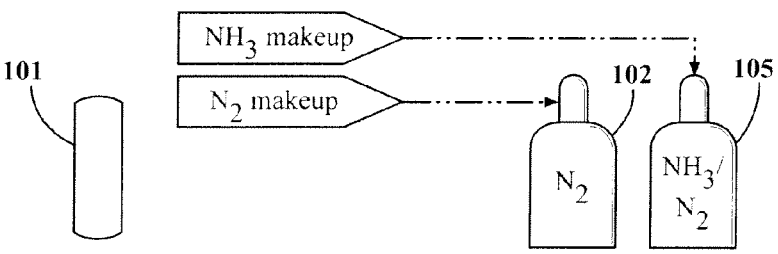

In FIG. 1E, desorption or purging of the first gas component is complete. Completion of desorption or purging can be indicted by change in pH or temperature similar to that described. However, the inverse change would be expected in that removal of the first gas component would cause a temperature decrease in the vessel 101. When desorption or purging is complete, the vessel can be opened and treated biomass removed. If desired, makeup gas can be added to tanks 102 and 105. The vessel 101 can be repacked with biomass material and the process repeated.

Example 2

One embodiment of the invention is exemplified in FIG. 2. In this embodiment, three vessels containing biomass material 201a-c are arranged in series.

Figure 2A:
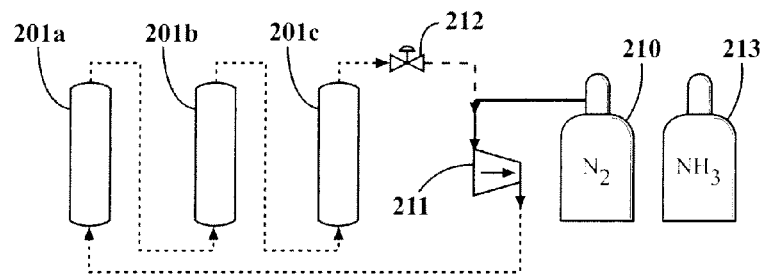
FIG. 2 is a flow diagram of an additional embodiment of the invention that incorporates the use of multiple vessels in series.

In FIG. 2A, water insoluble gas (e.g., nitrogen) is supplied from a tank 210 to the vessels by way of a compressor 211. Pressure is regulated by back pressure regulator 212.

Figure 2B:
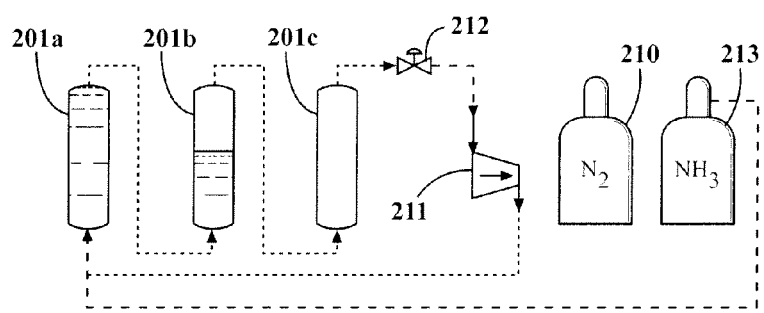

In FIG. 2B, vessel 201a is charged with water soluble gas (e.g., ammonia) from vessel 213 as the water insoluble gas continues to be circulated by way of compressor 211. The gases are mixed at the influent end of vessel 201a and feed to vessel 201a is continued in this manner until the biomass material is determined to be desirably saturated with water soluble gas. At such point, a breakthrough of water soluble gas is observed at the effluent end of the vessel 201a, and flow of the water soluble gas to the vessel is ceased. Any quantity of water soluble gas present in the effluent from vessel 201a is absorbed at the influent end of vessel 201b. The first gas component is allowed to remain in contact with the biomass material to treat the biomass material, such as for example to treat in a manner to achieve an increase in enzyme digestibility.

Figure 2C:
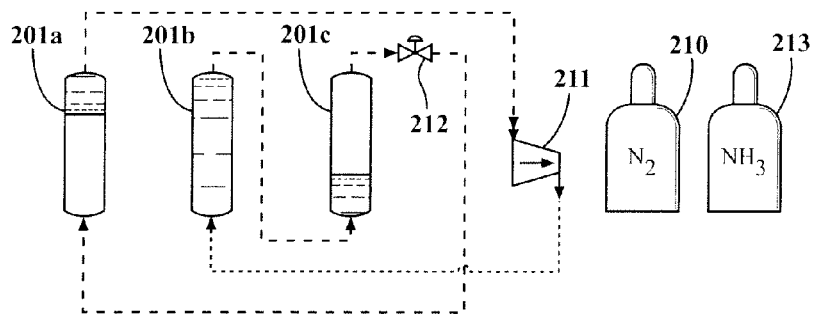

In FIG. 2C, vessel 201a is depressurized and partially desorbed or purged of the water soluble gas by purging with water insoluble gas from vessel 201c. As the water insoluble gas passes through the vessel 201a, the water soluble gas is desorbed or purged. As the mix of water soluble and water insoluble gases flow from vessel 201a, the mix is sent to vessel 201b, where the water soluble gas is absorbed by the biomass material. Once the biomass material in vessel 201b is saturated with water soluble gas, some water soluble gas exits from the effluent end of vessel 201b, and absorbs on the biomass material at the influent end of vessel 201c. Flow of water soluble gas to the vessel is ceased. The first gas component is allowed to remain in contact with the biomass material to treat the biomass material, such as for example to treat in a manner achieve an increase in enzyme digestibility.

Figure 2D:
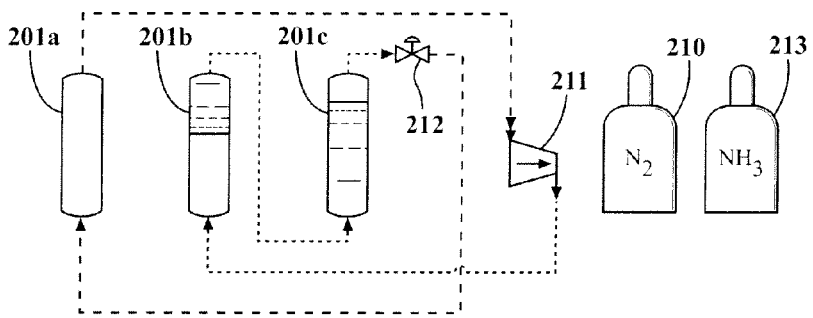

In FIG. 2D, circulation of water insoluble gas is resumed, until biomass material in vessel 201a is considered desorbed or purged, with vessel 201b being partially desorbed or purged, and vessel 201c not yet to the point of breakthrough. At this point, flow of gas may be stopped while vessel 201a is taken offline, unpacked of treated biomass material, repacked with untreated biomass material, and pressurized with water insoluble gas from vessel 201c.

Figure 2E:
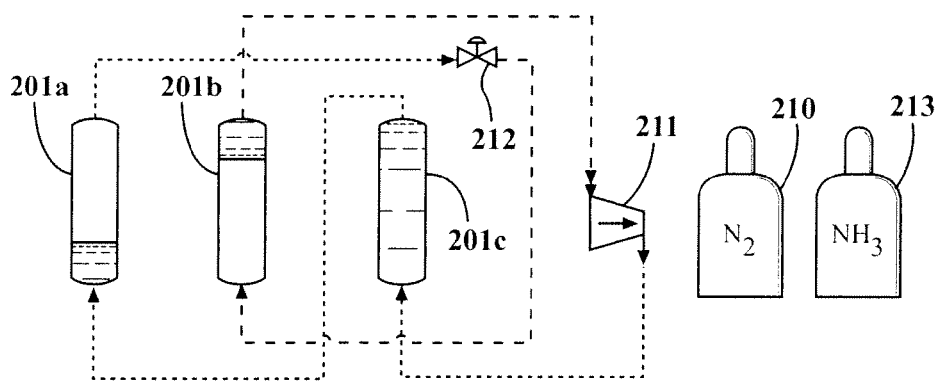

In FIG. 2E, vessel 201b is depressurized and partially desorbed or purged of water soluble gas by purging with water insoluble gas from vessel 201a, until the biomass material in vessel 201c becomes saturated with the water soluble gas. As before in the series, some water soluble gas breaks through vessel 201c to vessel 201a. Flow is stopped as before in the series to treat the biomass material in vessel 201c.

Figure 2F:
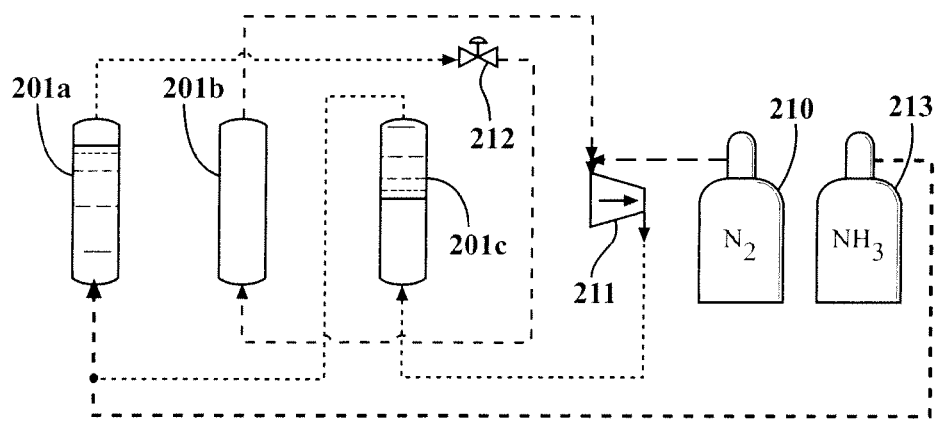

In FIG. 2F, water insoluble gas is recirculated until the biomass material in vessel 201b is purged or desorbed of water soluble gas. The treated biomass material in vessel 201b can then be unpacked and untreated biomass material can be packed into vessel 201b as previously done in series.

As shown in FIGS. 2A-F, multiple beds in series can be cyclically saturated and desorbed or purged of water soluble gas. The cycle can be repeated as often as desired, with makeup water soluble and water insoluble gas added as needed.

Example 3

Gas Separation Using a Packed Bed of Moist Wheat Straw as Biomass Material.

Wheat straw was ground to 2 mm maximum particle diameter. The moisture content of the ground straw was adjusted to 47 wt %. A stainless steel vessel, 53 cm in length, 3.5 cm internal diameter, 510 cubic centimeters internal volume, was packed with 91.0 grams of the ground, moist wheat straw. The vessel contained 48.0 grams of wheat straw dry matter and 43.0 grams of absorbed moisture. The vessel was packed by dumping the moist straw into the vessel, then tapping the outside of the vessel until no further settling of the biomass bed was observed. The bed was supported with 150-mesh stainless steel screen at both ends of the vessel. The vessel was then sealed, nitrogen circulated, and the vessel pressurized to 79±1 psig. Nitrogen sweep flow of 534 standard cubic centimeters per minute (sccm) was established through the pressurized vessel containing the packed straw, with the effluent sweep gas passing through a pressure reduction valve and bubbling at atmospheric pressure into a citric acid trap to determine ammonia content of the effluent gas.

A total of 8.5 grams of ammonia vapor from a bomb was mixed into the influent nitrogen sweep gas over a period of 16 minutes. As the ammonia/nitrogen mixture was contacted with the biomass bed, the outside of the inlet end of the vessel became quite warm, and the warm portion gradually spread axially to the middle of the vessel. After the ammonia had been charged to the bed, the nitrogen sweep gas flow was continued at 534 sccm and 79 psig, while the pH of the citric acid trap was monitored. As the nitrogen sweep flow continued, the outside of the influent end of the vessel became colder than ambient temperature.

Figure 3:
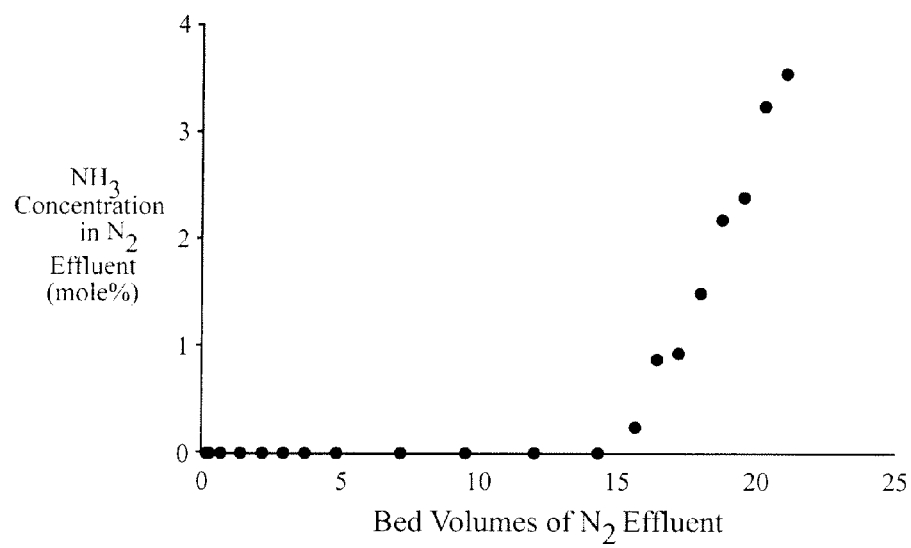
FIG. 3 is a graph showing one example of a breakthrough curve in which a water soluble gas is separated from an insoluble gas by absorption on a biomass material.

FIG. 3 shows ammonia concentration in the effluent gas. The data in FIG. 3 shows that at least 15 bed volumes of ammonia-free nitrogen eluted from the bed before ammonia breakthrough was observed. This result demonstrates effective absorption and separation of ammonia from nitrogen using a vessel containing a packed bed of moist wheat straw.

Example 4

An Absorption/Desorption Cycle Using a Vessel Containing a Wheat Straw Packed Bed.

Wheat straw was packed into a stainless steel vessel having the same dimensions as in Example 3, using the same packing technique. The total bed mass was 83.1 grams, and the moisture content of the straw was 39.5 wt %. A nitrogen sweep gas flow of 1 SLPM was established through the bed at 75 psig. A total of 19.0 grams of ammonia vapor was charged from a bomb into the vessel over a period of 5 minutes. As the ammonia was charged, the entire exterior surface of the vessel became hot, indicating that the ammonia was distributed throughout the biomass in the vessel.

The nitrogen sweep gas flow was then stopped, the vessel closed off, and allowed to equilibrate for 22 minutes. During this time the vessel pressure rose as high as 160 psig, and then gradually dropped as low as 140 psig. After equilibrating for 22 minutes, the vessel was depressurized by opening the outlet pressure reduction valve. A nitrogen sweep gas flow was ramped up to 28 SLPM at 15 psig. The influent nitrogen was heated in a gas heater to approximately 100° C. Ammonia concentration in the effluent gas was quantified by monitoring the pH of a citric acid trap through which the gas was bubbled. As the ammonia was desorbed from the biomass, the entire tube exterior became cold. The inlet end of the vessel gradually warmed due to inflow of heated nitrogen. Over a period of 18 minutes, the entire vessel exterior surface became warm.

Figure 4:
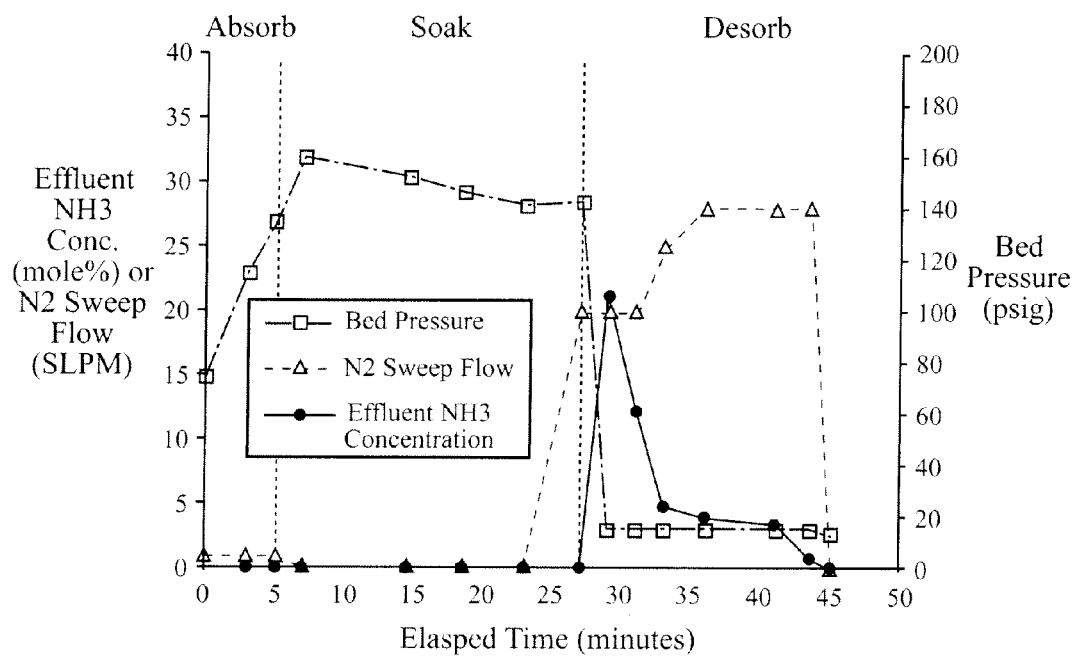
FIG. 4 is a graph of one example of the invention showing effluent concentration of water soluble gas, flow rate of water insoluble gas, vessel pressure during absorption, equilibration, and desorption stages of the example.

FIG. 4 shows the effluent ammonia concentration, nitrogen flow rate, and bed pressure during the absorption, equilibration (soak), and desorption stages of the experiment. Immediately after dropping the bed pressure and ramping up the nitrogen sweep gas flow, the ammonia concentration in the effluent rose to a peak of greater than 20 mole %, and then gradually tailed off to zero. The nitrogen flow was then stopped, and the biomass in the vessel was unpacked. There was no detectable odor of free ammonia remaining in the biomass after unpacking the bed. The moisture content of the straw after unpacking was 35.9 wt %, indicating that some minimal moisture loss occurred during the desorption stage. This example demonstrates that ammonia can be absorbed at elevated pressure onto a wheat straw packed bed in 5 minutes, allowed to soak or equilibrate on the bed for more than 20 minutes, and then desorbed from the bed at lowered pressure in less than 20 minutes, using heated nitrogen sweep gas.

Example 5

Enzyme Digestibility of Biomass after Gas Absorption/Desorption Cycle

Corn stover was ground in a Wiley mill to less than 2 mm particle size. Moisture content of the corn stover was adjusted to 45.2 wt %. The moist stover was then packed into a stainless steel vessel having the same dimensions as in Examples 3 and 4, using the same bed packing technique. The vessel contained a total of 85.7 grams of moist stover. The bed was pressurized to 175 psig with nitrogen sweep gas flowing at 3 SLPM. The vessel was then charged with 21.6 grams of ammonia vapor over a period of 10 minutes. During absorption vessel pressure rose as high as 203 psig. The biomass in the vessel was then allowed to soak or equilibrate for 20 minutes, during which time the vessel pressure dropped to 140 psig. The pressure was then reduced to 13 psig while heated nitrogen flow was ramped up to 30 SLPM. After 22 minutes of desorption, the entire vessel exterior was warm, indicating complete ammonia desorption, so the nitrogen flow was stopped. The biomass was then unpacked from the vessel. No detectable ammonia odor remained with the unpacked stover. Moisture content of the unpacked stover was 40.8 wt %.

Enzyme digestibility of a composite, treated stover sample for 72 hours at 50° C. using 15 Filter Paper Units (FPU) of cellulose enzyme activity and 42 Cellobiase Units (CBU) of cellobiase enzyme activity per gram of glucan gave 61% of theoretical glucose yield and 38% of theoretical xylose yield. For comparison, typical sugar yields from untreated corn stover are 26% glucose and 12% xylose. The sugar yields from the treated stover represent distinct improvements over untreated corn stover. This example demonstrates that ammonia can be absorbed at elevated pressure onto a packed bed of moist corn stover, and then desorbed completely from the bed of stover at reduced pressure, in a manner that improves the enzyme digestibility of the stover.

The principles and modes of operation of this invention have been described above with reference to various exemplary and preferred embodiments. As understood by those of skill in the art, the overall invention, as defined by the claims, encompasses other preferred embodiments not specifically enumerated herein.

The invention claimed is:

1. A method of removing at least one gas component of a gas stream to produce a conditioned cellulosic material, comprising: sending a feed gas stream comprised of a water soluble gas component having a Henry's Law constant ($K_H$) at 25° C. of at least 0.002 mole/L-atm and a water insoluble gas component having a Henry's Law constant ($K_H$) at 25° C. of less than 0.002 mole/L-atm to contact cellulosic material within a vessel; retaining at least a portion of the water soluble gas component within the vessel, as the water insoluble gas component of the feed gas stream is flowed through the vessel, to produce a conditioned cellulosic material having increased enzyme digestibility, wherein the conditioned cellulosic material having increased enzyme digestibility is a cellulosic material that is more readily converted to its constituent sugar components by hydrolytic enzymes relative to that of the cellulosic material initially supplied to the vessel; collecting an effluent stream from the vessel depleted in concentration of the water soluble gas component; ceasing collection of the effluent gas stream and sending a purge gas stream different in composition from that of the feed gas stream to the vessel to remove at least a portion of the water soluble gas component retained within the vessel; and removing the conditioned cellulosic material from the vessel.

2. The method of claim 1, wherein the collection of the effluent gas stream is ceased at a condition in which concentration of the water soluble gas component in the effluent stream becomes greater than a predetermined quantity.

3. The method of claim 2, wherein the collection of the effluent as stream is ceased at a point at which the effluent steam contains at least 0.1 mass % of the water soluble gas component, based on total mass of the effluent stream.

4. The method of claim 1, wherein the collection of the effluent gas stream is ceased at a condition at which temperature of the effluent stream is greater than that of the influent gas.

5. The method of claim 1, wherein the purge gas stream is comprised of at least 90 mass % water insoluble gas.

6. The method of claim 1, wherein the water soluble gas component is a base gas.

7. The method of claim 6, wherein the base gas is selected from the group consisting of ammonia, alkyl amines and pyridine.

8. The method of claim 1, wherein the water soluble gas component is an acid gas.

9. The method of claim 8, wherein the acid gas is selected from the group consisting of water soluble acid gases include, but are not limited to, nitric acid, hydrogen chloride, hydrogen peroxide, formaldehyde, acetic acid, nitrous acid, sulfur dioxide, hydrogen sulfide, carbon dioxide, carbon disulfide, hydrogen cyanide, carbonyl sulfide, methyl mercaptan and ethyl mercaptan.

10. The method of claim 1, wherein the feed as stream has a water soluble gas concentration of at least 1 mass %, based on total weight of the feed gas stream.

11. The method of claim 1, wherein the feed gas stream has a water insoluble gas concentration of at least 10 mass %, based on total weight of the feed gas stream.

12. The method of claim 1, wherein the water soluble gas component retained within the vessel increases enzyme digestibility of the cellulosic material by at least 5%.

13. The method of claim 1, wherein the cellulosic material contains at least 10 wt % water, based on total weight of the cellulosic material.

* * * * *